(12) United States Patent
John et al.

(10) Patent No.: US 12,156,936 B2
(45) Date of Patent: Dec. 3, 2024

(54) TOPICAL HERBAL COMPOSITIONS

(71) Applicant: CHEMISCHES LABORATORIUM DR. KURT RICHTER GMBH, Berlin (DE)

(72) Inventors: Sabrina John, Berlin (DE); Heiko Prade, Berlin (DE); Harald Van Der Hoeven, Berlin (DE)

(73) Assignee: CHEMISCHES LABORATORIUM DR. KURT RICHTER GMBH, Berlin (DE)

( * ) Notice: Subject to any disclaimer, the term of this patent is extended or adjusted under 35 U.S.C. 154(b) by 0 days.

(21) Appl. No.: 16/633,911

(22) PCT Filed: Jul. 26, 2017

(86) PCT No.: PCT/IB2017/000873
§ 371 (c)(1),
(2) Date: Jan. 24, 2020

(87) PCT Pub. No.: WO2019/021030
PCT Pub. Date: Jan. 31, 2019

(65) Prior Publication Data
US 2021/0085595 A1    Mar. 25, 2021

(51) Int. Cl.
| A61K 8/9789 | (2017.01) |
| A61K 8/02 | (2006.01) |
| A61K 8/04 | (2006.01) |
| A61K 8/06 | (2006.01) |
| A61P 7/10 | (2006.01) |
| A61Q 19/00 | (2006.01) |
| A61Q 19/08 | (2006.01) |

(52) U.S. Cl.
CPC .......... *A61K 8/9789* (2017.08); *A61K 8/0208* (2013.01); *A61K 8/0212* (2013.01); *A61K 8/0229* (2013.01); *A61K 8/042* (2013.01); *A61K 8/06* (2013.01)

(58) Field of Classification Search
CPC .... A61K 8/9789; A61K 8/0212; A61K 8/042; A61K 8/06; A61K 2236/31; A61K 36/28; A61K 2300/00; A61Q 19/08; A61Q 19/00; A61P 7/10; A61P 27/02
See application file for complete search history.

(56) References Cited

U.S. PATENT DOCUMENTS

| 5,869,031 A | 2/1999 | Tarroux et al. | |
| 6,159,487 A | 12/2000 | Znaiden et al. | |
| 2006/0280704 A1* | 12/2006 | John | A61Q 19/02 424/62 |
| 2008/0050459 A1 | 2/2008 | Elie et al. | |
| 2009/0028826 A1 | 1/2009 | Breton et al. | |
| 2016/0106793 A1* | 4/2016 | Peltier | A61K 31/197 424/93.4 |

FOREIGN PATENT DOCUMENTS

| CA | 2706992 A1 | 5/2010 |
| EP | 1737538 B1 | 10/2013 |
| EP | 4186498 A1 | 5/2023 |
| JP | 2007153822 A | 6/2007 |
| JP | 2007523830 A | 8/2007 |
| JP | 2011213699 A | 10/2011 |
| JP | 2012509257 A | 4/2012 |
| JP | 2013518911 A | 5/2013 |
| JP | 2014526537 A | 10/2014 |
| JP | 2016518425 A | 6/2016 |
| JP | 2016526901 A | 9/2016 |

OTHER PUBLICATIONS

E-Space English Language Abstract for JP 2007153822 A.
E-Space English Language Abstract for JP 2007523830 A.
E-Space English Language Abstract for JP 2012509257 A.
E-Space English Language Abstract for JP 2013518911 A.
E-Space English Language Abstract for JP 2014526537 A.
E-Space English Language Abstract for JP 2016518425 A.
E-Space English Language Abstract for JP 2016526901 A.
International Search Report for International Application No. PCT/IB2017/000873, mailed Apr. 23, 2018 (4 pages).
E-Space English Language Abstract for JP 2011213699.
International Preliminary Report on Patentability for International Application No. PCT/IB2017/000873, mailed Feb. 6, 2020, (10 pages).
Japanese Office Action, and English Translation thereof, for Japanese Application No. 2020-503931, mailed Nov. 12, 2021, (13 pages).
Karakas et al., "In vitro cytotoxic, antibacterial, anti-inflammatory and antioxidant activities and phenolic content in wild-grown flowers of common daisy—A medicinal plant," Journal of Herbal Medicine, vol. 8, pp. 31-39, 2017, (9 pages).

(Continued)

*Primary Examiner* — Mina Haghighatian
(74) *Attorney, Agent, or Firm* — Kagan Binder, PLLC

(57) ABSTRACT

The present invention provides topical formulations having an autophagy stimulating and/or heme oxygenase and activating/triggering effect on human skin for cosmetic and pharmaceutical use. Furthermore, the present invention provides topical formulations that trigger production of VEGF-C, reduce melanin synthesis and boost energy and cell function. Moreover, the present invention provides a new process for producing a herbal composition comprising a mixture of components of *Bellis perennis L.* and optionally *Hieracium pilosella* by aqueous extraction and the herbal composition comprising a mixture of components produced by the process of the present invention. The pharmaceutical formulations according to the present invention may be used for the treatment or prevention of dark circles under the eye and/or puffy eyes. The herbal composition according to the present invention may also be used in a cosmetic formulation for the cosmetic treatment or prevention of dark circles under the eye and/or puffy eyes.

20 Claims, 12 Drawing Sheets

(56) References Cited

OTHER PUBLICATIONS

Trouillas et al, "Antioxidant, anti-inflammatory and antiproliferative properties of sixteen water plant extracts used in the Limousin countryside as herbal teas," Food Chemistry, vol. 80, pp. 399-407, 2003, (9 pages).
Kasparova, "Seasonal Variation in the Haemolytic Activity of the Capitula of Bellis perennis L.," Ceska a Slovenska Farmacie, vol. 52, pp. 39-41, 2003, (English Abstract only) (4 pages).
The Encyclopedia of Medicinal Plants, Seibundo Shinkosha Publishing Co., Ltd., p. 218, 2000, (English translation of the column titled "Hieracium pilosella"), (4 pages).
Response to Opinion attached to European Search Report for European Application No. 17183285.0, filed Jul. 25, 2019, (6 pages).
Response to Communication Pursuant Article 94(3) EPC for European Application No. 17183285.0, filed Nov. 12, 2020, (9 pages).
Australian Office Action for Australian Application No. 2017425084, mailed Jul. 14, 2022, (8 pages).
"Osmanthus Fragrans Eye Patch", Company: Ba Wei Cosmetics, China, Brand: Doradosun Hydrating and Brightening Series, Published on Jun. 2016 MINTEL GNPD, <URL: https://www.gnpd.com/sinatra/recordpage/4068359>, Last Retrieved Jul. 13, 2022, (2 pages).
"Eye Gel", Company: Xshow Cosmetics Group, South Korea, Brand: Xshow Chamomile & Cucumber, Published on Jul. 2016 MINTEL GNPD, <URL: https://www.gnpd.com/sinatra/recordpage/4133171>, Last Retrieved Jul. 13, 2022, (2 pages).
"Eye Cream", Company: Laboratoires Galenic, France, Brand: Galenic Message, Published on May 2006 MINTEL GNPD, <URL: https://www.gnpd.com/sinatra/recordpage/527448>, Last Retrieved Jul. 13, 2022, (2 pages).
"Spécific Depigmentant", Company: Laboratoires Galénic, France, Brand: Galénic Message, Published on May 2000 MINTEL GNPD, <URL: https://www.gnpd.com/sinatra/recordpage/24091>, Last Retrieved Jul. 13, 2022, (1 page).
Oh, et al., "VEGF and VEGF-C: Specific Induction of Angiogenesis and Lymphangiogenesis in the Differentiated Avian Chorioallantoic Membrane," Developmental Biology 188, 96-109 (1997).
Huggenberger et al., "Stimulation of lymphangiogenesis via VEGFR-3 inhibits chronic skin inflammation," J. Exp. Med. vol. 207 No. 10 2255-2269 (2010).
Li et al., "ATP-driven and AMPK-independent autophagy in an early branching eukaryotic parasite," Autophagy, 2017, vol. 13, No. 4, 715-729.
Meçe, et al., "Lipid droplet degradation by autophagy connects mitochondria metabolism to Prox1-driven expression of lymphatic genes and lymphangiogenesis," Nature Communications | (2022) 13:2760 | https://doi.org/10.1038/s41467-022-30490-6 | www.nature.com/naturecommunications.
Creff et al., "Apelin-VEGF-C mRNA delivery as therapeutic for the treatment of secondary lymphedema," EMBO Molecular Medicine, vol. 16, ,pp. 386-415, Feb. 2024, (30 pages).
Murase et al., "Autophagy Has a Significant Role in Determining Skin Color by Regulating Melanosome Degradation in Keratinocytes," Journal of Investigative Dermatology, vol. 133, pp. 2416-2424, May 2013, (9 pages).
Shimizu et al., "Therapeutic Lymphangiogenesis Is a Promising Strategy for Secondary Lymphedema," International Journal of Molecular Sciences, 24(9):7774, Apr. 2023, (19 pages).
Lin et al., "VEGF-C/VEGFR-3 axis protects against pressure-overload induced cardiac dysfunction through regulation of lymphangiogenesis," Clin. Transl. Med., 11(3), 2011, (22 pages).

\* cited by examiner

F111 (herbal composition according to the present invention) promotes the expression of HO-1 by keratinocytes.

F111 (herbal composition according to the present invention) promotes the expression of HO-1, despite prolonged exposure to heme.

F111 (herbal composition according to the present invention) increases both metabolic activity and energy production in keratinocytes.

F111 (herbal composition according to the present invention) promotes autophagy.

F111 (herbal composition according to the present invention) reduces melanin production in epidermal skin models containing melanocytes, stressed by heme and UV radiation.

F111 (herbal composition according to the present invention) increases VEGF-C production by lymphatic endothelial cells.

F111 (herbal composition according to the present invention) increases VEGF-C production by lymphatic endothelial cells.

*In vivo results* t=0 t=56 days

3% F111 (herbal composition according to the present invention) performs better than placebo in reducing the surface area of dark circles.

t=0 t=56 days

3% F111 (herbal composition according to the present invention) performs better than placebo in reducing the surface area of dark circles.

t=0 t=56 days

3% F111 (herbal composition according to the present invention) performs better than placebo in reducing the surface area of dark circles.

F111 (herbal composition according to the present invention) leads to a stronger reduction of the surface area of dark circles than placebo.

F111 (herbal composition according to the present invention) leads to a stronger reduction of the color of dark circles than placebo.

TOPICAL HERBAL COMPOSITIONS

CROSS-REFERENCE TO RELATED APPLICATIONS

This application claims priority to International Application No. PCT/IB2017/000873, filed Jul. 26, 2017 and titled "TOPICAL HERBAL COMPOSITIONS," which is incorporated herein by reference in its entirety.

FIELD OF THE INVENTION

The present invention pertains to topical formulations having an autophagy stimulating and/or heme oxygenase and activating/triggering effect on human skin for cosmetic and pharmaceutical use. The topical formulations of the invention also trigger production of VEGF-C, reduce melanin synthesis and boost energy and cell function.

Moreover, the present invention also provides a new process for producing a herbal composition comprising a mixture of components of *Bellis perennis L.* and optionally *Hieracium pilosella* by aqueous extraction and the herbal composition comprising a mixture of components produced by the process of the present invention.

The pharmaceutical formulations according to the present invention may be used for the treatment or prevention of dark circles under the eye and/or puffy eyes.

The herbal composition according to the present invention may also be used in a cosmetic formulation for the cosmetic treatment or prevention of dark circles under the eye and/or puffy eyes

BACKGROUND OF THE INVENTION

Dark circles under the eyes are a common phenomenon. Dark circles make people look tired and older and can have significant impact on quality of life. Men and women are equally affected and, although aging plays a causative role, dark circles are seen at all ages.

The pathophysiology of dark circles is multifactorial and different physiological and pathophysiological processes as well as environmental stimuli may be implicated. In reducing the appearance of dark circles it is therefore essential to find common causes for the different processes which lead to the formation of dark circles. Aging related factors are important and need to be addressed, but the processes behind the daily fluctuations of dark circles are at least as important.

As set out below, various factors may contribute to the optical appearance of dark circles, which may include factors such as increased skin translucency, increased skin laxity and pigmentation, decreased lymphatic drainage and hemocongestion.

The skin under and around the eyes is particularly thin. The aging processes, both biological and accelerated by sunlight, play an important role in further thinning of the skin, where collagen and other components of the connective tissue are broken down, leading to the decline and destruction of the subcutis. Due to the decreasing thickness of the skin, the skin becomes increasingly translucent. This is a particular problem for the skin under the eyes, as here, we find a vast network of capillary blood vessels, lymph vessels and muscles just below the surface of the skin. As a consequence, thinning of skin leads to a darkened appearance, a factor playing an eminent role in the appearance of dark circles.

Due to aging, skin becomes lax and gravity will pull the lower eyelids down, leading to a shadowing effect, which is thus a further contributor to the appearance of dark circles. Additionally, due to the increase in skin laxity, skin becomes stretched and therefore even thinner and more translucent.

Damage, caused by UV light, can lead to hyperpigmentation. Especially people with a higher skin phototype often show a phenomenon called postinflammatory hyperpigmentation. This can play a prominent role in the appearance of dark circles.

The hyperpigmentary factor in the appearance of dark circles is not just an epidermal phenomenon. Dermal melanin deposition, where melanin-containing melanosomes have been engulfed in macrophages, resulting in the formation of so-called melanophages, is described to play an important role in the appearance of dark circles.

The most important function of the lymph vessels is to maintain a balance in fluid, macromolecules and oncotic pressure in the interstitial areas (extracellular space) of our body. They drain excess tissue fluid back to the blood circulation. Macromolecules and cells can directly enter the lymphatic vessels.

The lymphatic vessels become reduced in number and become increasingly hyperpermeable during the aging process as well as consequential to inflammatory processes. This results in edema of the lower eyelid, an accumulation of fluid. This fluid often takes on a purplish color and can significantly influence the color of skin under the eyes.

As mentioned above, another important factor in the etiology of dark circles, specifically related to aging, is dermal melanin deposition in melanophages. The cutaneous lymph vessels are extremely important in trafficking macrophages out of the skin. Melanophages are macrophages containing melanin, another illustration of the importance of the cutaneous lymphatic system in the appearance of dark circles.

Blood flow in the under eye-area is sluggish and slow. Hemocongestion, where blood flow is reduced to zero, is an often-occurring phenomenon in the skin under the eyes. Oxygenated hemoglobin has a reddish color and produces a pinkish tint in the skin. In contrast, deoxygenated hemoglobin has a purplish color and produced a tint which is more bluish. Hemocongestion is associated with a large presence of deoxygenated hemoglobin and strongly contributes to the appearance of dark circles.

Consequential to hemocongestion, but also to the inflammatory and aging processes, vascular permeability is increased. In the interstitial area in the dermis, the leaked red blood cells burst, releasing hemoglobin. The hemoglobin rapidly releases its heme group. The color of heme is very dark and can contribute to the appearance of dark circles significantly. Additionally, heme is a molecule which can induce a multitude of deleterious reactions in the dermis, many of them relevant for the formation and maintenance of dark circles.

Heme can cause cell damage, especially relevant for epithelial cells of both the cutaneous blood microvasculature and the lymph vessels. Heme induces oxidative stress, the breakdown of the extracellular matrix in the dermis (collagens, elastin, etc.) and stands at the beginning of inflammatory processes, supporting the pathophysiology of the formation of dark circles.

The inflammatory processes initiated by heme result in a further increase in permeability of both blood and lymph vessels. Heme is therefore a major contributing factor in the etiology of dark circles, both of the aging-related type and the acute type, the type which can change in appearance day to day.

Puffiness or bagginess under the eyes with associated discolorations also has many etiologic factors including an abnormal increase in leakage from capillaries beneath the surface of the skin. Fluid accumulating beneath the skin in the region under the eyes results in edema which manifests as baggy eyes often relatively darker in color. Puffy or baggy eyes are perceived as being cosmetically unacceptable or may be present to such an extent that therapeutic intervention is necessary. This may particularly be the case in connection with allergies, hay fever and the like.

The exact reasons for such increased capillary permeability is not always known, but several factors such as stress, allergic reactions, kidney malfunctions, high blood pressure, water retention, excessive consumption of caffeine and lack of sleep have been identified as being associated with the problem. Intrinsic aging and photodamage can also lead to similar changes.

It is the eyes that attract focal attention, and therefore it is desirable to avoid or reduce discoloration and puffy or baggy eyes in order to retain a cosmetically acceptable appearance.

People often resort to cosmetic surgery to remove bags beneath the eyes and restore the smoothness of the lower eyelids. The problems with cosmetic surgery include its great expense and risks of anesthesia and infection that accompany every surgical procedure.

Cosmetic products for application to the skin beneath the eye contain ingredients, such as plant extracts, aimed solely at making the lower eyelids feel comfortable and soothed. This merely amounts to relieving surface irritations, and does not address the cosmetic problems of the skin in order to restore elasticity and firmness to puffy skin beneath the eye.

Accordingly, there is a need for a product that is effective in (a) retarding formation of bags beneath the eyes, (b) partially or fully restoring a smooth skin contour to puffy skin beneath the eye, and (c) minimize dark circles under the eyes, thereby leading to a youthful appearance of the area around the eyes.

*Bellis perennis L.*, commonly known as English daisy or lawn daisy, belongs to the family of the Asteraceae.

It is widely used in homeopathy for treating different symptom complexes such as arthrosis, loss of appetite and sleeping disorders. Moreover, *Bellis perennis L.* is also traditionally used for the treatment of dermatological problems such as acne, eczema, badly healing wounds and deeper traumata of the tissue (see, e.g., H. A. Hoppe, Drogenkunde, Vol. 1, Angiospermen, 8. Edt., 1975; Dr. F. Losch, Krauterbuch; G. Leibold, Moderne Naturheilpraxis, Bassermann Verlag, 1993; M. Lange-Ernst, S. Ernst, Lexikon der Heilpflanzen, Honos Verlag; and W. D. Storl, Heilkrauter and Zauberpflanzen, A T Verlag, 2. Edt., 2000).

More recently *Bellis perennis L.* has been subject of pharmacological investigations, and particular ingredients, such as triterpene glycosides, have been identified to exhibit a broad pharmacological activity profile such as antifungal and antimicrobial, anticancerogenic and also post ischemic neuroprotective effects (see, e.g., DE 42 06 233; U.S. Pat. No. 6,444,233; G. Bader et al., Pharmazie 1990 July; 45(8); P. Avato et al.; Planta Med 1997 December; 63(6); and C. Desevedavy et al.; Journal Nat Prod 1989 January-February; 52(1)).

*Hieracium pilosella* (syn. *Pilosella officinarum*), also known as mouse-ear hawkweed, is a yellow-flowered species of flowering plant in the daisy family Asteraceae, native to Europe and northern Asia. It produces single, lemon-colored inflorescences. It is an allelopathic plant. Like most hawkweed species, it is highly variable and is a member of a species complex of several dozens of subspecies and hundreds of varieties and forms.

*Hieracium pilosella* contains umbelliferone, a compound similar to coumarin and a known antibiotic against brucellosis, as well as a frequent active compound in sunscreen lotions. The plant is also a potent diuretic and has been suggested/used as a further (adjuvating) component in formulations containing i. a. *Ruscus aculeatus*, caffeine tocopherol nicotinate, *Aesculus hippocastanum* or capsaicin, for the treatment of cellulite (WO 2004/110396, FR 2 729 856, WO 2012/052685).

EP 790 054 discloses compositions for topical treatment of skin problems associated with abnormal pigmentation. More particularly, this document focuses on the use of live yeast cell derivative in combination with a suitable vehicle, for treating discolorations and bagginess in facial skin below the eyes.)

U.S. Pat. No. 5,204,105 pertains to agents for reducing puffiness of the skin under the eyes and for reducing sensations of irritation and inflammation of the skin under the eyes selected from the group consisting of plant extracts and yeast extracts and combinations thereof. The plant extracts can comprise *Ruscus aculeatus* (butcher broom), hydrocotyl, *Aesculus hippocastanum* (horse chestnut), *Calendula officinalis* (calendula), *Hamamelis virginiana L.* (hamamelis, witch-hazel), *Equisetum arvense L.* (equisetum, horsetail), Euphrasia (eyebright), *Prunus persica* (peach), *Alchemilla vulgaris* (lady's mantle), *Hedera helix* (ivy), *Matricaria chamomilla* (German chamomile), and *Symphytum* (comfrey).

SUMMARY OF THE INVENTION

There is thus a need for compositions effectively reducing dark circles and also puffiness which focus on physiological events standing at the crossroads of the biological processes inducing the formation of dark circles and puffiness, such as heme.

The present invention provides pharmaceutical and cosmetic formulations particularly directed to satisfying this need. The formulations according to the present invention reduce puffy skin beneath the eye, smooth the contour of the skin, and reduce dark circles under the eye.

The herbal compositions and topical formulations according the present invention comprising components derived from *Bellis perennis* and *Hieracium pillosella*, address the most important aspects in the formation and the maintenance of dark circles.

The herbal composition according to the present invention induces the production of heme oxygenase and VEGF-C, activates autophagy and increases cellular functionality and energy. It also reduces melanin synthesis. The appearance of dark circles, their color and surface area are thus reduced, leading to a youthful appearance of the area around the eyes.

DETAILED DESCRIPTION OF THE INVENTION

Figure 1:
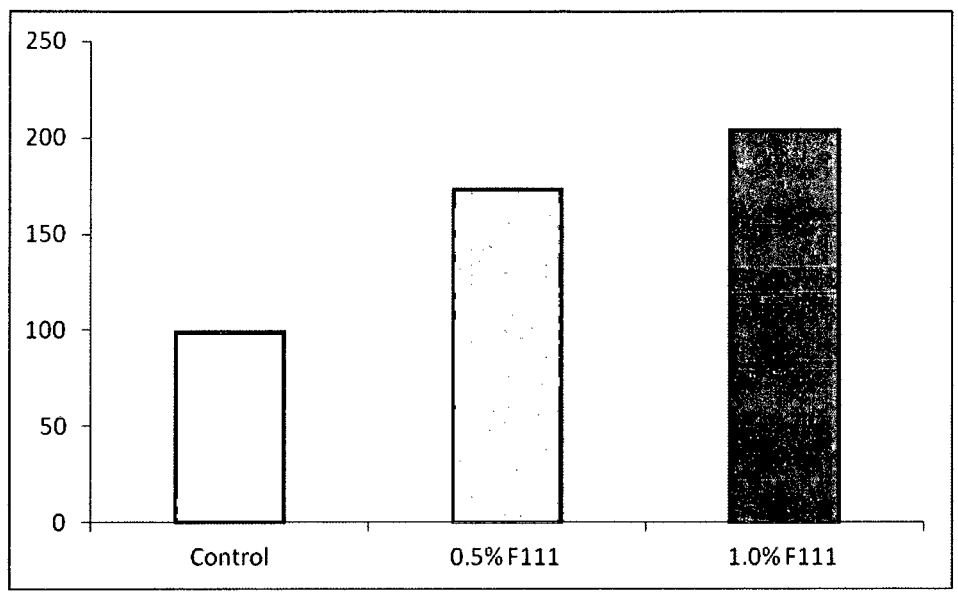
FIG. 1: Shows the promotion of the expression of HO-1 by keratinocytes by the herbal composition.

As already mentioned above, the present invention is based on the unexpected finding that components derived from *Bellis perennis* and *Hieracium pilosella* synergistically induce the production of heme oxygenase and VEGF-C, activate autophagy and increase cellular functionality and energy and also reduce melanin synthesis and as such are ideally suited for the treatment and prevention of dark circles under the eyes as well as puffiness.

Thus, the present invention in particular provides the following:

1. Pharmaceutical formulation comprising a mixture of components obtained from *Bellis perennis* and optionally *Hieracium pilosella* (herbal composition) for use in the treatment or prevention of dark circles under the eyes (periorbital dark circles, intraorbital venous stasis) and/or puffy eyes/puffiness (periorbital puffiness and/or periorbital edema).
2. Pharmaceutical formulation for use according to 1, wherein the dark circles under the eyes and/or puffiness are caused by any one of heredity, allergies, sleep deprivation/fatigue, oversleeping, eczema (atopic dermatitis), contact dermatitis, hay fever/allergic rhinitis, stress, thinning skin and/or loss of fat and collagen with age (ageing), iron deficiency (with or without anemia) or other iron diseases such as (juvenile) hemochromatosis, anemia of inflammatory response, minor trauma, crying, life style choices, fluid retention, excessive exposure to the sun, rubbing and scratching of eyes and medication.
3. Use of a composition comprising a mixture of components obtained from *Bellis perennis* and optionally *Hieracium pilosella* (herbal composition) for use in a cosmetic formulation for the cosmetic treatment of prevention of dark circles under the eyes (periorbital dark circles, intraorbital venous stasis) and/or puffy eyes/puffiness (periorbital puffiness and/or periorbital edema).
4. Use according to 3, wherein the dark circles under the eyes and or puffiness are caused by any one of thinning skin and/or loss of fat and collagen with age (ageing), life style choices, fluid retention, and influence of circadian rhythm by life style and life conditions.
5. A herbal composition comprising a mixture of components obtained from *Bellis perennis* and *Hieracium pilosella*.
6. Herbal composition according to 5, wherein the mixture of components obtained from *Bellis perennis* and *Hieracium pilosella* are present in a ratio of 1:1 to 9:1, 1:1 to 3:1, 1:1 to 5:2, 1:1 to 2:1 or 1:1 to 3:1 (w:w), preferably 1:1 or 3:1.
7. Herbal composition according to 5, having a pH-value of between about pH 3 to 7.5, preferably of about pH 4.0 to 6.5.
   In this context, it is noted that also the herbal composition according to any one of 1 to 4 has a pH-value of between about pH 3 to 7.5, preferably of about pH 4.0 to 6.5.
8. Formulation, composition or use according to any one of 1 to 7, wherein the mixtures of components are alcoholic, glycolic or aqueous extracts.
9. Formulation, composition or use according to any one of 1 to 7, wherein the mixtures of components are press juices (fresh plant juices).
10. Formulation, composition or use according to any one of 1 to 9, wherein the mixture of components obtained from *Bellis perennis* and *Hieracium pilosella* are prepared combined or separately.
    In this context, it is noted that in a preferred embodiment the mixture of components obtained from *Bellis perennis* and *Hieracium pilosella* are prepared separately and combined later, preferably at the ratios as stated in 6, above.
11. Formulation, composition or use according to any one of 1 to 10, wherein at least one of the mixture of components obtained from *Bellis perennis* and *Hieracium pilosella* or said active agent have been subjected to fermentation.
12. Formulation, composition or use according 11, wherein said fermentation is *Lactobacillus, Bifidobacter* or *Lactococcus* fermentation.
13. Composition according to any one of 5 to 12 for use in a pharmaceutical or cosmetic formulation.
14. Pharmaceutical, cosmetic formulation or use according to any one of 1 to 4 or 13 for topical application.
15. Embodiment according to 14, wherein said formulation is a cream, an ointment, an emulsion (milk), a tonic (lotion), stick, dispersion a formulation comprising a surfactant cleanser, a solution, a micellar water, a gel, a mask, a moist tissue pad or moist tissue mask.
16. Embodiment according to any one of 5 to 15, comprising 1 to 10% (w/w), 1 to 5% (w/w), 3 to 5% (w/w), 5% (w/w) or 3% (w/w) of the mixture of components obtained from *Bellis perennis* and *Hieracium pilosella* (herbal composition).
17. Embodiment according to any one of 5 to 15, comprising 1 to 50% (w/w), 1 to 30% (w/w), in particular 10 to 30% (w/w) of the mixture of components obtained from *Bellis perennis* and *Hieracium pilosella* (herbal composition).

HERBAL COMPOSITION ACCORDING TO THE INVENTION AND ITS PREPARATION

Herbal composition comprising mixture of components obtained from the plants according to the present invention.

The components are obtained from fresh or dried plant material of *Bellis perennis* and optionally *Hieracium pilosella*.

In a preferred embodiment the herbal composition comprises a mixture of components obtained from *Bellis perennis* and *Hieracium pilosella*.

*Bellis perennis*

The mixture of components obtained from *Bellis perennis* may be prepared from fresh or dried plant material such as flower heads, whole plant or aerial parts of the plant. The plant material may be milled, comminuted or used unground/unbroken.

The use of dried aerial parts of the plant or dried flower heads of *Bellis perennis* is preferred. Most preferred is the use of the dried and milled flower heads of *Bellis perennis*

*Hieracium pilosella*

The mixture of components obtained from *Hieracium pilosella* may be prepared from fresh or dried plant material such as flower heads, whole plant or aerial parts of the plant. The plant material may be milled, comminuted or used unground/unbroken.

The use of dried aerial parts of the plant or dried whole plant of *Hieracium pilosella* is preferred. Most preferred is the use of the dried and milled aerial parts of the plant of *Hieracium pilosella*.

The mixture of components obtained from *Bellis perennis* and *Hieracium pilosella*, respectively, may be prepared by any appropriate method known to the person of skills in the art.

Methods thus include solvent extraction, but also means other than solvent extraction, such as a (cold) pressed juice (fresh juice) obtained from fresh plant material by methods known to a person of skill in the art such using hydraulic presses (e.g., standard hydraulic cold-press technology with vertical pressing layers), roll mills or double screw juicers.

According to a preferred embodiment of the present invention, the components obtained from *Bellis perennis* and *Heracium pilosella* are obtained by the same type of process, preferably both by solvent extraction.

Solvent Extraction

According to the present invention, any extract of *Bellis perennis L.* and *Hieracium pilosella* obtained by decoction, digestion, percolation, soxlethtation, maceration or any other appropriate extraction method known to the person of skills in the art may be used.

Extraction Media

Suitable extraction media and solvents are water, aqueous buffers (such PBS or citrate buffer), glycols or glycol-water mixtures, alcohols or alcohol-water mixtures (e.g., 90:10 or 50:50), glycerin or glycerin-water mixtures.

Preferred extraction media/solvents are water or aqueous buffers, ethanol ethanol-water mixtures, and methanol or methanol-water mixtures. Additionally, also extracts obtained by extraction with glycols like propylene glycol, butylenes glycol or water mixtures thereof having preferably a water content of 5 to 60% may be used according to the present invention. The use of citrate buffer pH 5.0 is preferred.

In a more preferred embodiment, a sodium-citrate buffer according to Sörensen (buffer containing 0.1 M disodium citrate and 0.1 N HCl, having a pH between 1.2 and 5.0, preferably between 2.0 and 5.0, most preferred pH 3.0) is used. In a further preferred embodiment, a phosphate buffer according to Sorensen (0.06 M potassium phosphate and 0.06 M disodium phosphate, pH range 5 to 8, preferably pH 5) is used.

In an even more preferred embodiment, a sodium citrate buffer according to Sörensen with 0.1 M citric acid monohydrate ($C_6H_8O_7xH_2O$) and 0.1 M trisodium citrate dihydrate solution having a pH of 5.0 is used.

Ratio Drug and Extraction Medium

The proportion between drug and extraction medium (solvent) ranges from 1:100 (1% w/w) to 20:100 (20% w/w), 1:100 (1% w/w) to 50:100 (50% w/w) preferred from 3:100 to 10:100 or 3:100 to 30:100, more preferred from 5:100 to 10:100 or 5:100 to 7:100.

It is particularly preferred that the proportion between drug and extraction medium is between 5:100 and 10:100, preferably 5:100 to 7:100.

Ratio of Components in the Herbal Composition

According to the present invention, the mixture of components obtained from *Bellis perennis* and *Hieracium pilosella* are present in the herbal composition in a ratio (*Bellis:Hieracium*) in the range of 1:1 to 1:9, preferably 1:1 to 3:1 or 1:1 to 5:2, more preferably 1:1 to 2:1 or 1:1 to 3:1, most preferred with respect to activity and/or stability are 1:1 and 3:1.

PH Value of the Final Herbal Composition

The herbal composition of the present invention has a pH value of between about pH 3 and pH 7, preferably in the range of pH 4.0 and pH 6.5.

As stated above, the herbal composition according to the present invention comprising a mixture of components obtained from *Bellis perennis* and *Hieracium pilosella* which may be prepared by separate preparation from the respective plant (i.e. obtaining the components from each plant separately and combining the obtained mixtures of components afterwards) or by obtaining the mixture of components jointly from a mixture of the starting plants.

A further object of the present invention is to provide a process for producing an aqueous extract of *Bellis perennis L.* and an extract obtained by that process.

The mixture of components obtained from *Bellis perennis* may i. a. be obtained in accordance with the process and methods disclosed in EP 1 737 538.

According to the invention, the extraction time and temperature may vary depending on the extraction media, particularly an extraction time between 1 h and 10 days. More particularly, a time between 1 h and 24 h, 2 h and 8 h, 1 h and 4 h or 2 h and 4 h is preferred.

The temperature may range between 20° C. and 100° C., preferably between 25° C. and 85° C. or between 25° C. and 60° C.

In a particularly preferred embodiment of the present invention, *Bellis perennis* and *Hieracium pilosella* are separately extracted with citrate buffer pH 5.0, such as the Sorensen citrate buffer described above.

Exemplary Process

It is particularly preferred that *Bellis perennis* (in particular dried flower heads of *Bellis perennis*) are extracted with citrate buffer pH 5.0 at a temperature of 60° C. for 4 to 8 hours, whereby the proportion of drug (i.e. plant):extraction medium is 7:100 (7%) to 10:100 (10%). After extraction the plant material is separated from the liquid phase, e.g., by a decanter CA 22 (Westfalia Seperator AG).

It is, moreover, particularly preferred that *Hieracium pilosella* (in particular the dried whole aerial part of the plant) are extracted with citrate buffer pH 5.0 at a temperature of 25° C. to 60° C. for 2 to 4 hours., whereby the proportion of drug:extraction medium is 5:100 (5%) to 7:100 (7%). The crude extract is then fractionated by ultrafiltration (MW cut-off: 100 kDa) to obtain the <100 kDa fraction.

The <100 kDa fraction is used for preparing the herbal composition by combining it with the mixture of components obtained from *Bellis perennis* at the ratio in accordance with the present invention.

Preservation of the Herbal Composition

The herbal composition according to the present invention may be expediently preserved by the addition of preservatives commonly used in the art such as sodium dehydroacetate, 2-hydroxybenzoic acid, 1-phenyl-1-propanol, Dermosoft® 700B (mixture of levulinic acid; sodium levulinate; glycerin and water), phenethyl alcohol or sodium benzoate at concentrations commonly known in the art such as 0.02% (w/w), 0.2% 0.3% (w/w), 0.5% (w/w) 0.85% (w/w) and 0.5% (w/w), respectively.

The use of sodium dehydroacetate and/or sodium benzoate is particularly preferred, whereby a concentration in the range of 0.2% and 0.5% (w/w) is preferred.

Stabilisation of the Herbal Composition by Fermentation

In a further embodiment of the present invention, at least one of the mixtures of components obtained from *Bellis perennis* and *Hieracium pilosella* or the herbal composition may optionally be subjected to fermentation.

The such obtained herbal composition may exhibit an enhanced stability and activity, such as enhanced endothelin-1 activity.

It is preferable that said fermentation is *Lactobacillus*, *Bifidobacter* or *Lactococcus* fermentation.

To this effect the following subspecies are preferred:
*Bifidobacter* sp. *longum*, *Lactococcus* sp. *Lactis* and *Lactobacillus* sp. *Helveticus*.

For the fermentation according to the present invention the bacteria of choice are first cultivated in a nutrition medium in order to obtain an inoculum which is then added to a liquid mixture of components obtained from from *Bellis perennis* and/or *Hieracium pilosella* or the herbal composition.

The fermentation is carried out under anaerob conditions for about 24 to 48 hours at a temperature of about 32 to 37° C.

Fermentation is stopped by inactivation of the bacteria by pasteurization, such as heat inactivation of the bacteria at 85° C. for about 45 min.

The following process serves for illustrative purposes only and should not be construed to be limiting.

Exemplary Fermentation Process

*Lactococcus* sp. were cultivated in nutrition medium having the following composition:

|  | (g/l) |
| --- | --- |
| Wheat Pepton | 7.0 |
| Yeast extract | 3 |
| $K_2HPO_4$ | 2 |

-continued

|  | (g/l) |
| --- | --- |
| NaCl p.A. | 1 |
| Glucose Monohydrate | 5.5 |
| Fructose | 5 |
| Water | 976.5 |
| +trace elements solution | 1 |
| total | 1000.00 |

Trace elements solution:

|  | g/20 ml |
| --- | --- |
| $MgSO_4 \times 7H_2O$ | 1.333 |
| $MnCl_2 \times 4H_2O$ | 0.293 |
| Water | 18.37 |

An extract of *Bellis perennis* and *Hieracium pilosella* was prepared by (e.g.) 10% dried drug in water for 1 hour at 95° C. or in accordance with the processes above by combined or separate extraction, preferably by combined extraction.

The biomass was separated and the liquid phase served as the nutrition medium for the bacteria. In a further embodiment, biomass and liquid phase were not separated after extraction and the obtained suspension served as the nutrition medium for the bacteria.

Fermentation under anaerobic conditions was carried out for 48 hours at 36° C. using a *Lactobacillus* inoculum. After this time the fermentation was finished by heat inactivation of the bacteria (45 minutes, at 85° C.).

CHARACTERIZATION OF THE HERBAL COMPOSITION

Characterization of Herbal Composition by LC-HRMS

Qualitative characterization of the herbal composition of the invention by its components was carried out by liquid chromatography high resolution mass spectrometry (LC-HRMS).

In short, the herbal composition of the invention was diluted in water and analyzed by a reversed-phase capillary liquid chromatography system (Dionex Ultimate 3,000 NCS-3500RS Nano, Thermo Scientific) connected to an Orbitrap Fusion mass spectrometer (Thermo Scientific).

In a preferred embodiment, the herbal composition according to the present invention (such as F111) comprises the following components as shown in Table 1, below:

TABLE 1

Preferred qualitative composition of the herbal composition of the invention

| Compound/components | mass $[M + H]^+$ | Herbal composition according to the present invention |
| --- | --- | --- |
| Chlorogenic acid | 353.0867 | x |
| Anthocyanidines |  |  |
| Cyanidin 3-malonylglucoside | 535.1082 | x |
| Cyanidin 3-glucuronylglucoside |  |  |

TABLE 1-continued

Preferred qualitative composition of the herbal composition of the invention

| Compound/components | mass [M + H]⁺ | Herbal composition according to the present invention |
|---|---|---|
| Flavonoides | | |
| Apigeninhexoside | 433.1129 | x |
| Apigeninglucuronide | 447.0922 | x |
| Apigeninmethylglucuronide | 461.1078 | x |
| Kaempferolhexoside | 449.1078 | x |
| Quercetinhexoside | 465.1027 | x |
| Isorhamnetinhexoside | 479.1184 | x |
| Apigeninglucoside | 489.1027 | x |
| Isorhamnetinglucuronide | 493.0977 | x |
| Isorhamnetinglucoside | 565.1188 | x |
| Isorhamnetin | | x |
| Saponines | | |
| Perennisoside III, IV, V, VI | 1163.5844 | x |
| Perennisoside XII | 1121.5738 | x |
| Perennisoside XIII | 1207.6106 | x |
| Perennisoside XIV | 1283.6266 | x |
| Perennisoside XV | 1369.6634 | x |
| Perennisoside XVIII & XIX | 1105.5789 | x |
| Desacyl-perennisoside I, II & III | 959.5210 | x |
| Desacyl-perennisoside VIII & IX | 1105.5789 | x |
| Desacyl-perennisoside X & XI | 1283.6266 | x |

The saponine compounds shown in Table 2, below, are optional components of the herbal compositions according to the present invention:

TABLE 2

Optional components of the herbal composition of the invention

| Compound/components | mass [M + H]⁺ |
|---|---|
| Saponines | |
| Bellisisosides C & E | 1307.6630 |
| Bellisisoside D | 1349.6736 |
| Perennisosides I & II | 1043.5421 |
| Perennisoside VII | 1205.5950 |
| Perennisosides VIII & IX | 1189.6000 |
| Perennisosides X & XI | 1367.6478 |
| Perennisosides XVI | 1325.6372 |
| Perennisaponine A | 1159.5895 |
| Perennisaponines G; H | 1305.6474 |

DRY CONTENT OF THE HERBAL COMPOSITION OF THE INVENTION

The herbal composition of the present invention is characterized by a dry content (incl. buffering agent and preservative) of about 3.5% to 5.5%, preferably about 4%. The dry water content was determined by the modified official method for the determination of water content according to the Official Collection, § 35 LMBG (German Law on Food and Consumer Goods) L 02.06-2 (EC).

The separate mixture of components obtained from *Bellis perennis* (i.e. prior to combination with the components of *Hieracium pilosella*) is characterized by a dry content (incl. buffering agent and preservatives) of about 4.3 to 5.3%, preferably of about 4.7%.

The separate mixture of components obtained from *Hieracium pilosella* (i.e. prior to combination with the components of *Bellis perennis*) is characterized by a dry content (incl. buffering agent and preservative) of about 3.3 to 4.3%, preferably of about 3.7%.

PARTICULARLY PREFERRED EMBODIMENT

A preferred embodiment of the herbal composition according the present invention is referred to in the present application as "F111" (INCI Name: *Hieracium Pilosella* (Hawkweed) Extract, *Bellis Perennis* (Daisy) Flower Extract).

This preferred embodiment is prepared by separate extraction with citrate buffer according to Sörensen (0.1 M citric acid monohydrate and 0.1 M trisodium citrate dehydrate) having a pH of 5.0 using the extraction methods described above.

This herbal composition exhibits a pH range of 4.0-6.5, and may preferably be preserved with preserving agents such a sodium dehydroacetate and/or sodium benzoate at concentrations commonly used in the art. It may be incorporated in a pharmaceutical/cosmetic composition/formulation preferably at a concentration of 3-5% (w/w) of the total weight of the total formulation.

INDICATIONS

Therapeutic Application

The pharmaceutical formulation according the present invention may be used in a therapeutic method of treating or preventing dark circles under the eyes (periorbital dark circles, periorbital hyperpigmentation, intraorbital venous stasis) and/or puffy eyes/puffiness (periorbital puffiness and/or periorbital edema).

The dark circles under the eyes and or puffiness may be caused by any one of heredity, allergies, sleep deprivation/fatigue, oversleeping, eczema (atopic dermatitis), contact dermatitis, hay fever/allergic rhinitis, stress, thinning skin and/or loss of fat and collagen with age (ageing), iron deficiency, minor trauma, crying, life style choices, fluid retention, skin pigmentation abnormalities (especially black and Asian people), excessive exposure to the sun, rubbing and scratching of eyes and medication.

Cosmetic Application

The cosmetic formulation according to the present invention may be used in a cosmetic method for the treatment or prevention of dark circles under the eyes and/or puffy eyes.

The dark circles under the eyes and or puffiness may be caused by any one of heredity, allergies, sleep deprivation/fatigue, oversleeping, eczema (atopic dermatitis), contact dermatitis, hay fever/allergic rhinitis, stress, thinning skin and/or loss of fat and collagen with age (ageing), iron deficiency, minor trauma, crying, life style choices, fluid retention, skin pigmentation abnormalities (especially black and Asian people), excessive exposure to the sun, rubbing and scratching of eyes and medication.

Preferred indications for the cosmetic formulation are dark circles under the eyes and puffiness due to thinning skin and/or loss of fat and collagen with age (ageing), life style choices, fluid retention, skin pigmentation abnormalities (especially black and Asian people), influence of circadian rhythm by life style and life conditions.

Other preferred cosmetic indications are dark circles under the eyes and puffiness due to sleep deprivation/fatigue, oversleeping, excessive exposure to the sun.

TESTING OF THE COMPOSITION COMPRISING A MIXTURE OF COMPONENTS OF THE PLANTS ACCORDING TO THE PRESENT INVENTION (HERBAL COMPOSITION ACCORDING TO THE PRESENT INVENTION)

Efficacy Studies In Vitro Assays

The following studies have been carried out with a herbal composition according to the present invention, hereinafter called "F111", without preservatives.

"F111" may be characterized as follows:

| INCI Name | CAS No. | EINECS No. |
|---|---|---|
| Hieracium Pilosella (Hawkweed) Extract (EU Name: Hieracium Pilosella Extract) | 84012-22-6 | 281-668-2 |
| Bellis Perennis (Daisy) Flower Extract (EU Name: Bellis Perennis Extract) | 84776-11-4 | 283-935-9 |

| Analytical Data | |
|---|---|
| Refractive index nD20 | 1.3389 |
| Density 20° C. | 1.0191 g/ml |
| pH value | 4.8 |
| Polyphenols | 1850 mg/ml |
| Dry residue (with buffer, without preservatives) (2 h, 102° C.) | 3.6% |
| Color value (Gardner) | 6.8 |

EXAMPLES

If not described otherwise, the data of the cell based assays have been normalized with the cell count obtained by DAPI staining.

1. Heme Oxygenase (HO-1)

Heme is broken down by Heme Oxygenase (HO-1). HO-1 is an enzyme strongly involved in the skin's defense mechanisms against oxidative stress. Heme is broken down by HO-1 to obtain biliverdin and biliverdin can be further broken down by biliverdin reductase to bilirubin. Heme is dark colored, biliverdin is rather greenish and bilirubin is yellowish.

HO-1 is inducible and produced by, for instance, by keratinocytes. Inducing HO-1 in keratinocytes is therefore an interesting approach towards accelerating the breakdown of heme. On top of the above-mentioned effects on skin color, the breakdown of heme is of great importance in stopping the progression of the deleterious processes induced by heme, as described above.

Method

Human Keratinocytes (HaCaT) were treated with the test compounds (PBS and F111, respectively) for 48 hours. Determination of HO-1 was performed by ELISA (R&D Systems, Inc.; KCB3776). Relative fluorescence units were determined at 540 nm (ex.)/600 nm (em.). Non-treated cells are set at 100%.

Results

At different concentrations, F111 strongly promotes the production of HO-1 by immortalized keratinocytes (HaCaT) (FIG. 1). This indicates that F111 promotes heme degradation and supports one of the most important processes which act against the formation of dark circles.

2. Heme and HO-1 expression

Heme is pro-oxidative and pro-inflammatory. The presence of heme, therefore, can have a negative impact on skin cell functionality. As keratinocytes have the ability to produce HO-1, and can be exposed to heme, it is therefore important to verify that the effect of heme on HO-1 production by keratinocytes is not influenced negatively.

Method

Human Keratinocytes (HaCaT) were pretreated with F111 for 24 hours. Heme (5 µM) was added for different periods of time. The determination of HO-1 was performed by ELISA (R&D Systems, Inc.; KCB3776). Relative fluorescence units were determined at 540 nm (ex.)/600 nm (em.). Non-treated cells are set at 100%.

Results

Figure 2:
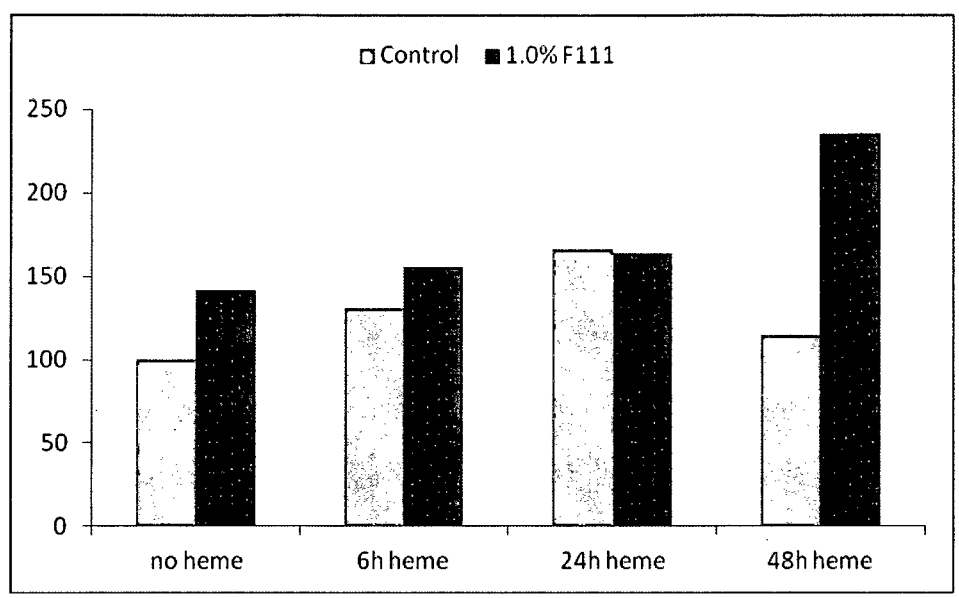
FIG. 2: Shows the promotion of the expression of HO-1, despite prolonged exposure to heme by the herbal composition.

Heme treatment of immortalized keratinocytes (HaCaT) cells, at first, leads to an increase of production of HO-1, but prolonged exposure (48 h) to heme leads to a clear reduction of production of HO-1 (FIG. 2). As heme is proinflammatory and pro-oxidative, this is likely a result of the prolonged stress the cells are exposed to. F111 allows the cells to deal with the presence of heme, leading to an increased production of HO-1 after prolonged exposure to heme. This is contrary to untreated control cells. This experiment mimics the in vivo situation in dark circles where prolonged heme exposure can have deleterious effect on the skin cells and F111 shows here that it can compensate effectively for these effects.

Heme Oxygenase 1 (HO-1) Assay for Demonstration of Synergistic Effect

The inventors of the present invention conducted heme oxygenase 1 (HO-1) assays to demonstrate the synergistic effect provided by the combined components obtained from *Bellis perennis* and *Hieracium pilosella* (such as F111) as compared to the effects provided by the separate extracts of *Bellis perennis* and *Hieracium pilosella*.

The separate extracts of *Bellis perennis* and *Hieracium pilosella* were prepared with Sorensen citrate buffer pH 5.0 in accordance with the processes described above for the composition in accordance with the present invention, albeit the resulting liquid phases were not combined.

Method

Human Keratinocytes (HaCaT) were pretreated with *Hieracium pilosella* extract or *Bellis perennis* extract or with F111 for 24 hours. Heme (5 µM) was added for different periods of time. The determination of HO-1 was performed by DuoSet®IC total Heme Oxygenase 1 ELISA (R&D Systems, Inc.; DYC3776-2). Absorbance was determined at 450 nm (ex.)/570 nm (em.).

Non-treated cells were set at 100%.

Results

Synergystic effect promotes the expression of HO-1 on human keratinocytes after heme exposure (see Table 3, below)

The basal expression of HO-1 in keratinocytes is not inducible by treatment with *Hieracium pilosella* in lower concentrations.

A pronounced expression of HO-1 can be observed after application of an extract of BeHis perennis at all concentrations.

Treatment with F111 induced an even higher expression of HO-1, indicating a synergistic effect.

This effect is even more pronounced in the presence of damaging heme, in particular at 48 hours.

TABLE 3

Synergistic effect of F111 promoting the expression of HO-1 in human keratinocytes

| | | HO-1 no Hemin | | | HO-1 24 h Hemin | | | HO-1 48 h Hemin | | |
|---|---|---|---|---|---|---|---|---|---|---|
| | % w/w | mean | SD | % CV | mean | SD | % CV | mean | SD | % CV |
| Control | PBS | 100.0 | 10.6 | 10.6 | 161.3 | 9.7 | 6.0 | 164.4 | 25.1 | 13.3 |
| H. pilosella | 0.25% | 93.5 | 11.5 | 12.3 | 127.8 | 12.1 | 9.5 | 189.7 | 9.6 | 3.9 |
| B. perennis | 0.25% | 237.6 | 9.5 | 4.0 | 272.8 | 23.1 | 8.5 | 470.1 | 25.6 | 5.4 |
| F111 | 0.25% | 248.2 | 12.4 | 5.0 | 338.2 | 6.3 | 2.2 | 690.6 | 42.8 | 7.7 |
| H. pilosella | 0.50% | 100.6 | 8.9 | 8.9 | 126.6 | 9.6 | 7.6 | 223.5 | 21.4 | 8.0 |
| B. perennis | 0.50% | 248.1 | 7.3 | 2.9 | 271.7 | 10.8 | 4.0 | 493.4 | 27.9 | 5.7 |
| F111 | 0.50% | 282.6 | 16.6 | 6.4 | 395.9 | 18.8 | 6.1 | 742.0 | 13.8 | 2.1 |
| H. pilosella | 0.75% | 120.4 | 3.4 | 2.8 | 158.3 | 4.5 | 2.8 | 233.5 | 13.4 | 5.0 |
| B. perennis | 0.75% | 304.8 | 7.5 | 2.5 | 337.4 | 3.1 | 0.9 | 603.0 | 34.3 | 5.7 |
| F111 | 0.75% | 317.5 | 8.1 | 2.5 | 516.1 | 3.5 | 1.0 | 842.1 | 58.6 | 10.6 |

3. Cellular Energy and Metabolic Turnover

Functionality of the skin cells, keratinocytes from the epidermis in particular, suffers with age and under inflammatory circumstances. Keratinocytes play an essential role in cell signaling. With that they stand at the basis of cell signaling towards the dermal compartment, the area in the skin where we find the extracellular matrix (collagens etc.) and blood and lymph vessels. Loss in keratinocyte functionality can have a negative impact on the structures in the dermal compartment and should therefore be addressed.

Method

Human Keratinocytes (HaCaT) were pretreated with F111 for 24 hours. Determination of ATP was performed by Luminescent Adenosine Triphosphate Detection Assay (Packard Instrument Company, Inc.; 6016541). The luminescence was determined in a luminescence reader (Spectramax Paradigm, Molecular Devices, LLC.). The metabolic activity was measured by tetrazolium salt (MTT) assay. The absorbance was determined in a microplate reader (Spectramax Paradigm, Molecular Devices, LLC.) at 570 nm. Non-treated cells served as controls and were set to 100%.

Results

Figure 3:
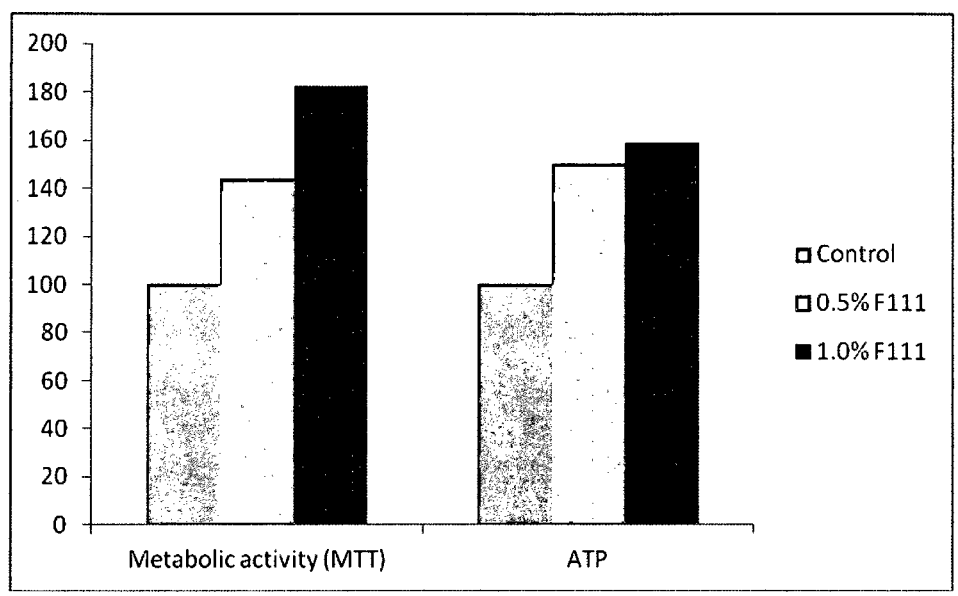
FIG. 3: Shows the increase of both metabolic activity and energy production in keratinocytes by the herbal composition.

F111 at both 0.5% and 1.0% leads to an increase of metabolic activity and ATP (energy) production by immortalized keratinocytes (HaCaT) (FIG. 3). F111, therefore, shows to have a positive influence on these cells, increasing their functionality and health. At least part of the results obtained here can be attributed to the influence of F111 on autophagy, described below. One of the key features in dark circles is cellular stress, which can have a significant impact on cell functionality. The results from this experiment show that F111 supports the skin cells in compensating for this stress.

4. Autophagy

Autophagy is a process with which cells can recycle old dysfunctional organelles and protein aggregates. The accumulation of such 'cellular waste' is an important feature in cellular aging. Induction of autophagy, therefore, is a sensible anti-aging approach, which increases cellular longevity and functionality.

Autophagy plays another important role in the context of dark circles. It is a process with which keratinocytes degrade melanin-containing melanosomes. In this role, autophagy is described to be an important determinant in regulating skin color and induction of autophagy is, therefore, a sensible approach to lighten skin.

Method

Human Keratinocytes (HaCaT) were pretreated with F111 for 24 hours. Cells were treated with 2 µM Chloroquine (inhibition of Autophagy flux). Cells were incubated for further 48 hours w/wo F111. Determination of LC3B was performed by ELISA using LC3B (D11) XP® Rabbit mA (New England Biolabs, Inc.). The detection antibody was an Anti-Rabbit IgG (H+L), F(ab')2 Fragment (Alexa®488) (New England Biolabs, Inc.). The fluorescence was measured at 485 nm (excitation) and 535 nm (emission) in fluorescence reader (Spectramax Paradigm, Molecular Devices, LLC.).

Results

Figure 4:
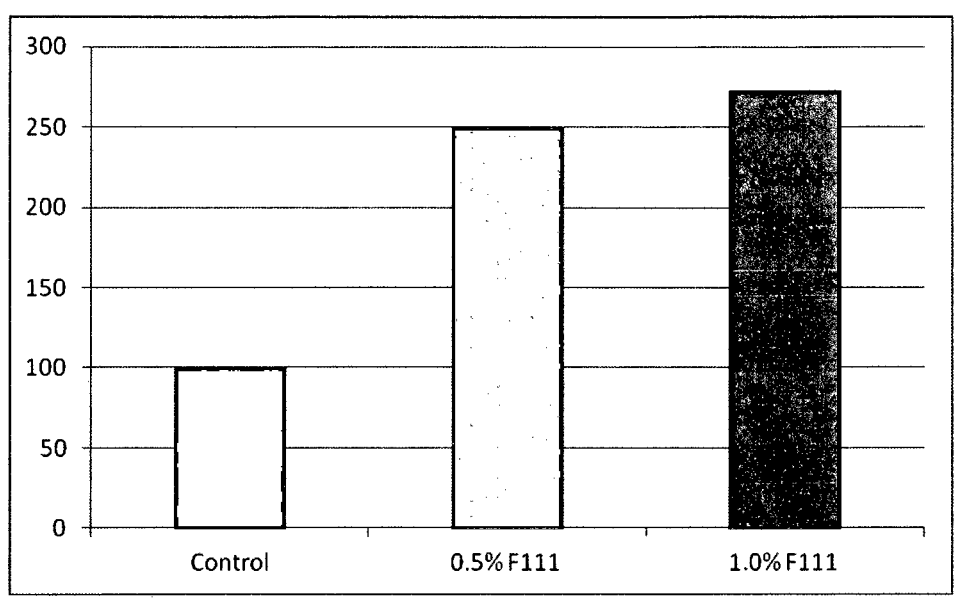
FIG. 4: Shows the promotion of autophagy by the herbal composition.

F111 at both 0.5% and 1.0% strongly induces autophagy in immortalized keratinocytes (HaCaT) (FIG. 4). This indicates that it strongly supports the cellular anti-aging processes and can increase cellular functionality (as proven above). With this activity F111 supports the cellular processes in breaking down melanosomes, leading to skin lightening activities.

5. Melanogenesis under the Influence of Heme and UV Radiation

Pigmentation, both aging-related or consequential to inflammatory processes, plays an important role in the appearance of dark circles. It is therefore opportune to study the effect of an active ingredient on this phenomenon in more detail. Heme, being pro-inflammatory and pro-oxidative, and playing an important role as a 'motor' behind the processes involved in the formation of dark circles, can be considered to be an inducer of melanogenesis, specifically related to dark circles. Obviously, UV radiation is an important inducer of melanogenesis too. Like heme, UV light is an inducer of inflammatory and oxidative processes in the skin. It is therefore of interest to study whether the treatment with heme and heme together with UV radiation has an influence on melanin synthesis and if an active ingredient can reduce this.

Method

Week 1: Human epidermal equivalents with melanocytes (epiCS-M, CellSystems GmbH) were treated for one week with 10 µM heme on the basolateral side. Some of the skin models were irradiated with 0.3 J/cm$^2$ UVA+0.03 J/cm$^2$ UVB one time daily. Week 2: Heme treatment and irradiation was stopped and the models were treated (apical) with either water (control) or 3% F111 (in water) for 7 days. Melanin content of the skin models was extracted and quantified by a photometric method.

Results

Figure 5:
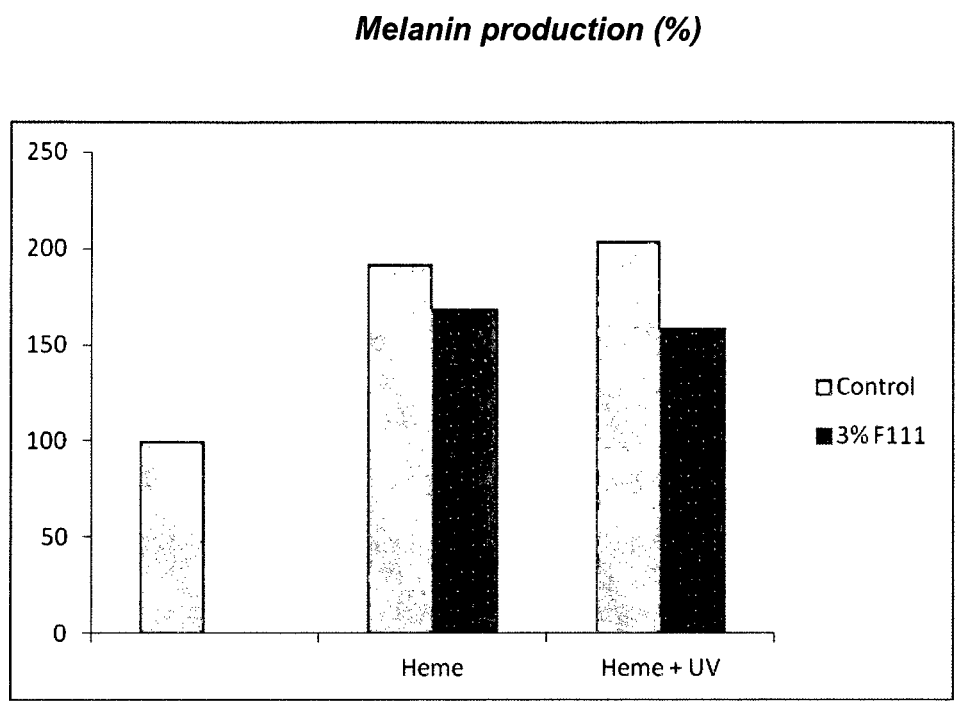
FIG. 5; Shows the reduction of melanin production in epidermal skin models containing melanocytes, stressed by heme and UV radiation by the herbal composition.

Human epidermal equivalents with melanocytes, exposed to heme, clearly show an increased production of melanin. In this setting, the treatment with F111 shows a clear reduction of melanin production (FIG. 5). Exposure of these epidermal skin equivalents to both heme and UV radiation, shows a further increase in melanin production. Here, the treatment with F111 shows a reduction of melanin production even larger than with the exposure to heme only. These results clearly demonstrate that F111 reduces melanin production under circumstances which are extremely relevant to the formation and maintenance of dark circles.

6. VEGF-C, Lymphatic Endothelial Cells and Keratinocytes

VEGF-C is a growth factor which promotes the production of functional lymphatic vessels. These are of eminent importance in the etiology of dark circles, as described above. Induction of the production of VEGF-C is therefore extremely important in fighting dark circles. In the eye area the accumulation of fluid takes place relatively rapidly. This fluid contains cells, ions and macromolecules, proteins specifically. The ions lead to an osmotic pressure, whereas the proteins lead to a phenomenon called oncotic pressure. Oncotic pressure can be described as a type of osmotic pressure which is induced by proteins. In an experiment where the effect of an active ingredient of VEGF-C expression is determined, osmotic pressure should therefore be taken into account. As keratinocytes play an essential role in cellular communication, including towards the lymphatic endothelial cells, it is of particular interest to analyze the effect of an active ingredient in an experimental design where the effect of keratinocyte communication to lymphatic endothelial cells, relevant to VEGF-C expression, is determined.

Method

In an in vitro situation, keratinocytes release their mediators into the cell culture medium. This medium can be transferred to lymphatic endothelial cells and their ability to express VEGF-C can be determined. Human Keratinocytes (HaCaT) were pretreated with F111 for 24 hours. Osmolarity of the medium was adjusted by NaCl solution and cells were incubated for a further 24 hours.

The medium was transferred to the human dermal lymphatic endothelial cells (HDLEC), which were further incubated for 24 hours. The determination of VEGF-C was performed by ELISA (R&D Systems, Inc.; #DVEC00). Absorbance was measured ad 450 nm/540 nm. Non treated, non-damaged cells served as controls and were set to 100%.

Results

Figure 6:
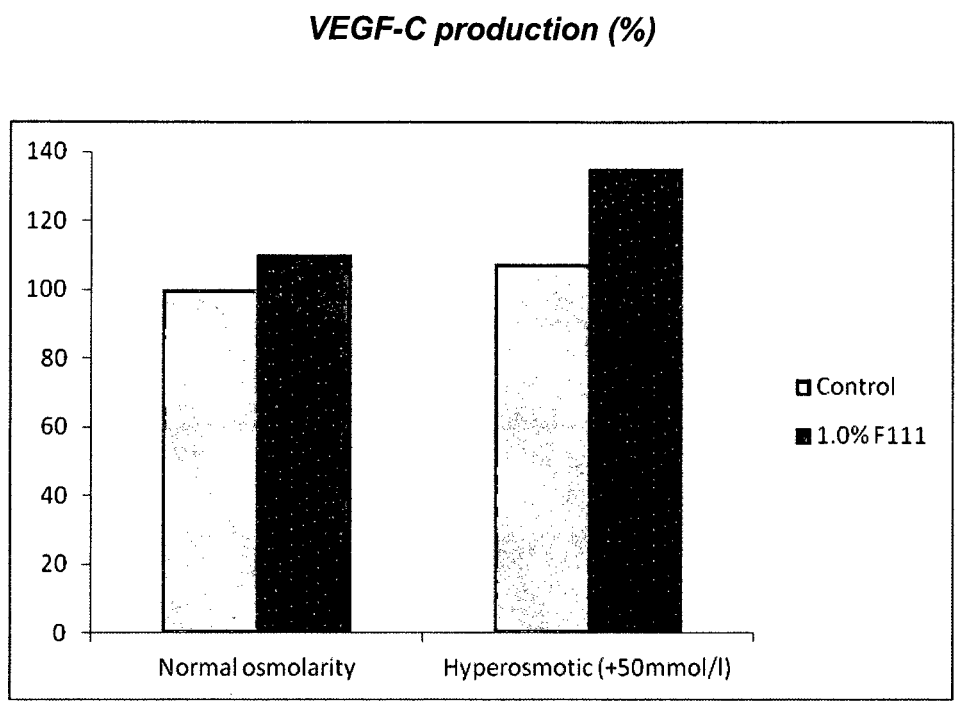
FIG. 6: Shows the increases of VEGF-C production by lymphatic endothelial cells by the herbal composition.

Osmotic pressure is stressful for keratinocytes. The cultivation of lymphatic endothelial cells in a medium which originates from hyperosmotically stressed keratinocytes leads to a slight increase in VEGF-C (FIG. 6). In an identical setting, now including the treatment of the keratinocytes by F111, a much clearer increase in VEGF-C production by lymphatic endothelial cells can be observed.

Cultivation of the lymphatic endothelial vessels in a medium originating from the treatment of keratinocytes at normal osmolarity and in the presence of F111, also increases VEGF-C production, albeit slightly. These results indicate that F111 supports the formation of new and functional lymph vessels. With this action, F111 plays an important role in the promotion of drainage of excess fluid, inflammatory cells and heme from the interstitial area in the dermis, an activity which is essential in fighting dark circles.

7. VEGF-C, TGF-β and Lymphatic Endothelial Cells

TGF-β is an important growth factor in the management of the dermal structure. It induces the production of, for instance, collagens, elastin and hyaluronic acid and it plays a pivotal role in maintaining skin firmness, elasticity and thickness. Its production is reduced in aged skin, however. As the loss of dermal structure leads to an increase in skin laxity and translucency, TGF-β is an important factor to take into account. However, in the area under the eyes, the hyperosmotic environment caused by leakage of plasma, proteins and cells into the interstitial area, TGF-β has an important negative influence; it reduces the expression of VEGF-C by lymphatic endothelial cells. TGF-β is an essential growth factor for dermal quality, but its negative influence on VEGF-C expression under hyperosmotic pressure should be compensated for.

Method

Human dermal lymphatic endothelial cells (HDLEC) were pretreated with F111 for 24 hours. Osmolarity of the medium was adjusted by NaCl solution. Incubation w/wo TGF-β commenced for another 24 hours. The determination of VEGF-C was performed by ELISA (R&D Systems, Inc.; #DVEC00). Absorbance was measured at 450 nm/540 nm. Non-treated, non-damaged cells served as controls and were set to 100%.

Results

Figure 7:
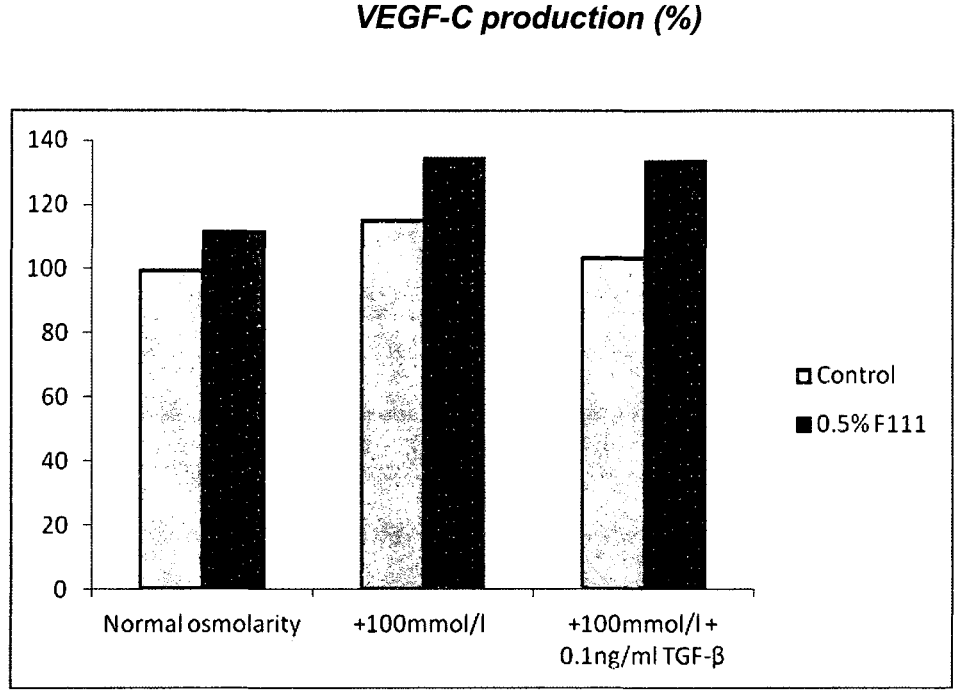
FIG. 7: Shows the increases of VEGF-C production by lymphatic endothelial cells by the herbal composition under influence of TGF-β.
Figure 8A:
FIG. 8: Shows that the herbal composition performs better than placebo in reducing the surface area of dark circles (in vivo).
Figure 8A:
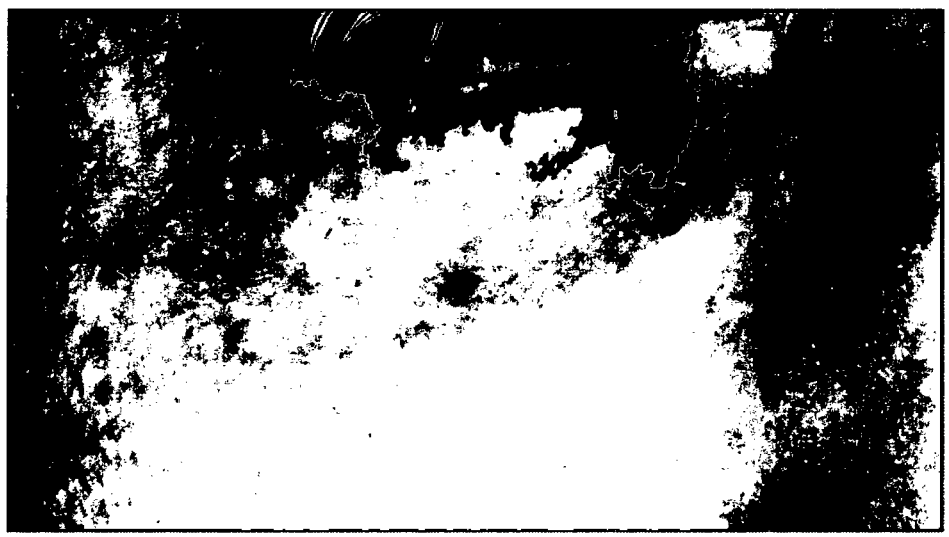
Figure 8B:
Figure 8B:
Figure 8C:
Figure 8C:
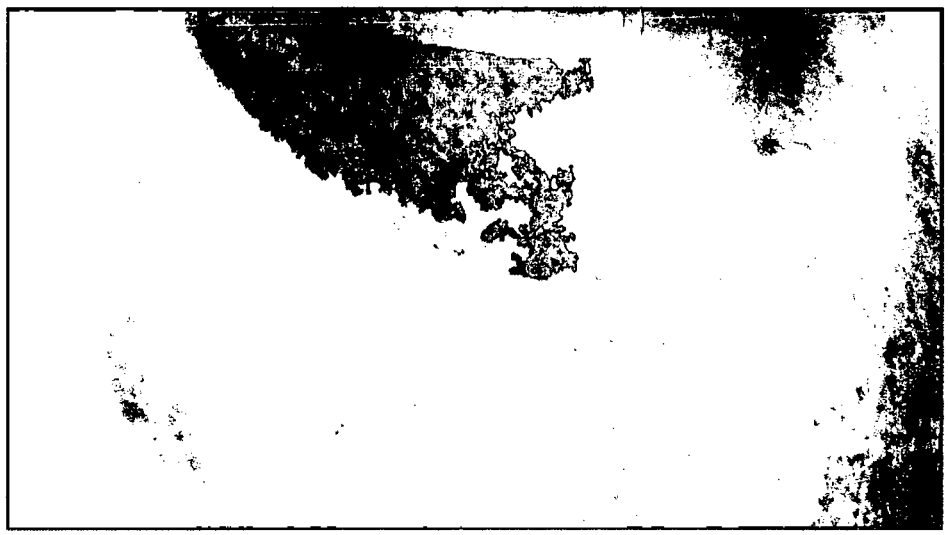

An increase in osmolarity leads to an increase in VEGF-C expression by lymphatic endothelial cells. The treatment of TGF-β leads to a reduction of VEGF-C expression, similar to the cells not exposed to hyperosmotic stress. TGF-β therefore exerts an important negative effect and prevents lymphangiogenesis. The treatment with F111 under hyperosmotic pressure leads to an increase in expression of VEGF-C. Interestingly, F111 strongly compensates for the negative effects of TGF-β (FIG. 7). The positive and relevant influence on new lymph vessel production by F111, with this, is further underlined.

DAPI Cell Staining

Cell staining with DAPI (4',6-diamidino-2-phenylindol) is a measure of cell count and served for cell count correction.

DAPI is a fluorescent dye that is used in fluorescence microscopy to label DNA. The compound accumulates preferentially to AT-rich regions in the minor groove of DNA. When excited with ultraviolet light, DAPI fluoresces with blue to cyan color. In connection with double-stranded DNA, the absorption maximum is at a wavelength of 358 nm, the emission maximum at 461 nm.

Cells were grown and treated as described in the methods referred to above. A methanol solution with 0.0005% DAPI was applied to the cell layer for 15 minutes at 37° C. Subsequently, the cells were washed with double distilled water and the microtiter plate was allowed to dry for 30 minutes at 37° C.

The fluorescence was measured at 355 nm (excitation) and 600 nm (emission) in a fluorescence reader (Fluoroscan Ascent FL; Labsystems).

Figure 9:
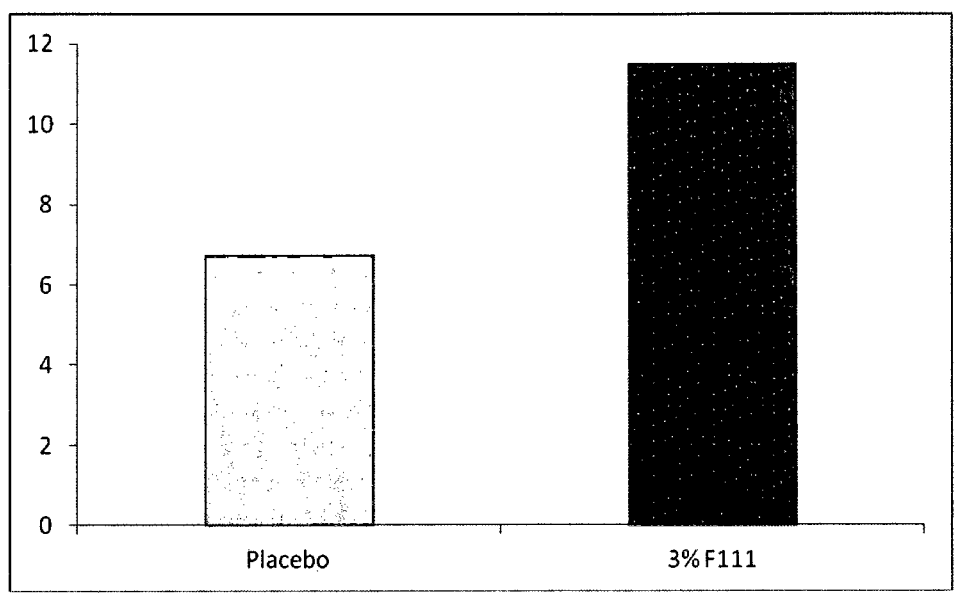
FIG. 9: Shows that the herbal composition leads to a stronger reduction of the surface area of dark circles than placebo. Results obtained on 12 volunteers, after 56 days, twice daily application (in vivo).
Figure 10:
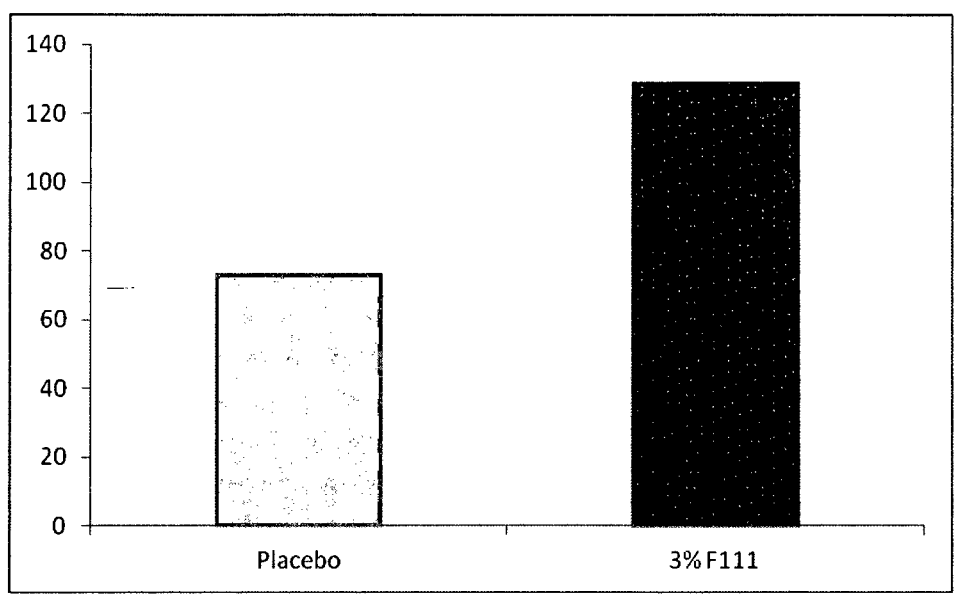
FIG. 10: Shows that the herbal composition leads to a stronger reduction of the color of dark circles than placebo. Results obtained on 12 volunteers, after 56 days, twice daily application (in vivo).

Efficacy Studies—In Vivo Assays (FIGS. 8-10)

The following studies have been carried out with a herbal composition according to the present invention, hereinafter called "F111", with preservatives "F111" may be characterized as follows:

| INCI Name | CAS No. | EINECS No. |
|---|---|---|
| Hieracium Pilosella (Hawkweed) Extract (EU Name: Hieracium Pilosella Extract) | 84012-22-6 | 281-668-2 |
| (Daisy) Flower Extract (EU Name: Bellis Perennis Extract) | 84776-11-4 | 283-935-9 |

| Analytical Data | |
| --- | --- |
| Refractive index nD20 | 1.335-1.345 |
| Density 20° C. | 1.015-1.025 g/ml |
| pH value | 4.0-5.5 |
| Dry residue (with buffer and preservatives) (2 h, 102° C.) | 3.8-4.8% |
| Color value (Gardner) | 6-12.5 |
| Sodium Benzoate | 0.40-0.55% |
| Sodium Dehydroacetate | 0.10-0.20% |

Reduction of Dark Circles

In order to assess whether F111 reduces dark circles a study was performed where 12 volunteers applied cosmetic formulations, one containing 3% F111 and a corresponding placebo, for 56 days, twice daily on each of the eye areas. At the beginning of the study and after 56 days of applying the cosmetic products, standardized photographs were taken by the use of a VISIA® device (Canfield Scientific, Inc.). This device allows for detailed imaging in a standardized environment, disallowing external light influences. This allows for the comparison of different pictures of the same person at different time points.

The standardized photographs were then digitally analyzed by Newtone Technologies (Lyon, France). By making use of the combined technologies offered by Canfield and Newtone conclusions can be drawn on the effect of a cosmetic product on dark circles.

Through the digital analysis of the photographs important parameters relevant to dark circles are generated, for instance, the so-called ITA° (Individual Typological Angle). The ITA° is a parameter relevant for darkness of skin. Overall a reduction of dark circles is obtained when ITA° increases in value.

An essential feature in the reduction of dark circles is their surface area. A reduction of the surface area of dark circles plays an extraordinarily important role in the visibility of dark circles.

Results

Individual results show that the application of 3% F111 for 56 days clearly leads to a reduction of the surface area of dark circles (FIG. 8)

An analysis of the effects obtained with 3% F111 and placebo formulation, now with a focus on the actual surface area of the dark circles on all individuals (FIG. 9), clearly show that 3% F111 reduces the surface area of the dark circles more effectively than placebo.

To further underline the effects of F111 on dark circles an additional analysis was made on the parameters relevant to their color and visibility. The application of a formulation containing 3% F111 leads to an increase in value of the parameter ITA°, clearly larger than obtained with placebo (FIG. 10).

COSMESTIC OR PHARMACEUTICAL FORMULATIONS OF THE INVENTION

The compositions comprising the mixtures of components of said plants (herbal compositions) according to the present invention can be administered by any means which causes contact between said mixtures and the site of action in a mammal's body, preferably being that of a human being, and the form of a cosmetic or pharmaceutical formulation which contains them.

According to the present invention, cosmetic and pharmaceutical formulations for topical application and the topical application of the formulations according to the present invention are particularly preferred.

Thus, the present invention further provides pharmaceutical and cosmetic formulations suitable for topical/dermatological application (around the area of the human eye) comprising the (herbal) compositions according to the present invention.

The (herbal) compositions according to the present invention may be included in common cosmetic and pharmaceutical formulations known to the person of ordinary skills in the art (see, e.g., Bauer et al., Pharmazeutische Technologie, 5. Edt. Govi-Verlag Frankfurt, 1997; Rudolf Voigt, Pharmazeutische Technologie, 9. Edt., Deutscher Apotheker Verlag Stuttgart, 2000), such as O/W and W/O creams, O/W and W/O emulsions (milk), ointments, tonic (lotion), gels, multiple emulsions (W/O/W and O/W/O), cosmetic dispersions (hydrodispersions and lipodispersions), sticks, formulations comprising a tenside, in particular a surfactant cleanser, simple solutions (oily or aqueous), a micellar water or a mask.

The cosmetic or pharmaceutical formulation according to the present invention preferably is an emulsified base, in particular O/W creams and O/W emulsions or a gel, in particular a hydrogel, and is particularly suitable for treatment of the skin under the eyes.

The herbal compositions of the present invention may also be incorporated into cosmetic or pharmaceutical delivery systems and/or sustained release systems.

Examples of delivery systems or sustained release systems include, without limitation, liposomes, mixed liposomes, oleosomes, nicosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres, nanospheres, liposheres, millicacpsules, microcapsules, nanocapsules as well as microemulsions and nanoemulsions.

The compositions/herbal compositions according to the present invention can also be incorporated in/absorbed to fabric, non-woven fabric or tissue or cotton wool balls or pads and may thus be, e.g., applied in form of a moist tissue pad or moist tissue mask.

The formulations according to the present invention may also be packaged in soft gelatine capsules or sachets for single use dosage units.

The cosmetically or/and pharmaceutically effective amount of the herbal compositions of the invention which should be administered, as well as their dosage, will depend on numerous factors, including age, state of the patient, the nature or severity of the condition, disorder or disease to be treated or cared for, the route an frequency of administration and of the particular nature of the herbal composition to be used.

Cosmetically or/and pharmaceutically effective amount is understood to mean a non-toxic but sufficient amount of the herbal composition to provide the desired effect.

The herbal compositions of the present invention are used in the cosmetic or pharmaceutical formulation of the invention at cosmetically or pharmaceutically effective concentrations to achieve the desired effect.

As a rule the topical formulations according to the present inventions may comprise 1 to 50% (w/w) with regard to the total weight of the formulation of the (herbal) composition according to the present invention.

In patch tests concentrations up to 50% (w/w) have not shown to elicit any skin irritation.

For cosmetic formulations a concentration of about 1 to 10% (w/w), 1 to 5% (w/w), 3 to 5% (w/w), 5% (w/w) or 3% (w/w) of the mixture of the components of *Bellis perennis* (and *Hieracium pilosella*) (the herbal composition) is preferred. A concentration of 3-5% (w/w) is particularly preferred.

In particular, pharmaceutical formulations may comprise a higher concentration of 1 to 30%, 10 to 30% but may also preferably comprise a concentration of about 1 to 10% (w/w), 1 to 5% (w/w), 3 to 5% (w/w), 5% (w/w) or 3% (w/w) of the mixture of the components of *Bellis perennis* (and *Hieracium pilosella*) (the herbal composition).

The cosmetic and pharmaceutical formulations according to the present invention, in addition to the usual excipients well known to a person of skill in the art, may comprise additional ingredients such as:

Ingredients for Enhancing Firmness and Elasticity

The agents for enhancing firmness and elasticity of the skin and for minimizing under eye circles can be selected from the group consisting of collagen inducers and silicon derivatives. Preferred are collagen inducers such as milk peptide complex (MPC) at a concentration range of about 0.2 to about 2.0%, preferably at a concentration at about 0.5 to 1.9%. Further preferred is a silicon derivative that comprises a complex of methylsilanol elastinate and methylsilanol aspartate hydroxyprolinate. The concentration of this complex in the emulsified cosmetic composition can range from 3.4% to 4.6%. Four percent is the preferred concentration. The preferred respective weight ratios of methylsilanol elastinate and methylsilanol asparatate hydroxyprolinate in the complex are 25% and 75%. A commercial source of methylsilanol elastinate and methylsilanol aspartate hydroxyprolinate is Exsymol S.A.M. (Monte Carol, Monaco). Methylsilanol elastinate is sold under the trade name of "Proteosilane-C" and methylsilanol aspartate hydroxyprolinate is sold under the trade name of "Hydroxyprolisilane-C.

Ingredients for Reducing Effects of Free-Radicals

The anti-free radical ingredients of a emulsified cosmetic composition can be selected form the group consisting of derivatives of vitamins C or E, selenium metal compounds, or beta carotene derivatives.

Preservatives

Preservatives are used to prevent the growth of microbes. A sufficient quantity of one or more preservatives thus may be added. The topical formulations according the present invention may thus contain one or more preservatives commonly known in the art such as sodium dehydroacetate, 2-hydroxybenzoic acid, 1-phenyl-1-propanol, Dermosoft® 700B (mixture of levulinic acid; sodium levulinate; glycerin and water), phenethyl alcohol or sodium benzoate at concentrations commonly used in the art.

Antioxidants

To maintain the composition's color and prevent malodorous developments, an antioxidant may be included in the cosmetic and pharmaceutical compositions. The antioxidant can be an ascorbyl ester selected from the group consisting of ascorbyl palmitate, ascorbyl myristate, and ascorbyl stearate. A preferred antioxidant is ascorbyl palmitate.

Emulsifiers

Emulsifiers serve two functions. They act like a solubilizing agent to combine the water soluble and non-water soluble phases together; that is, form a stable bridge between the waters and the oils of the ingredients. The emulsifiers also serve as emollients, providing a pleasant, aesthetically appropriate, tactile feeling when the emulsified composition is applied to the skin. These can be propylene glycol isoceteth-3 actetate and laureth-2 benzoate. One of the emulsifiers can be an ester of an unsaturated fatty acid selected from the group consisting of of isodecyl oleate, isononyl oleate, isoundecyl oleate, isononyl elaidate, isodecyl elaidate, isoundecyl elaidate, isononyl vaccenate, isodecyl vaccenate, and isoundecyl vaccenate. A preferred ester of an unsaturated fatty acid is isodecyl oleate.

Another emulsifier can be an ester of a short-chain saturated fatty acid selected from the group consisting of myristyl octanoate, myristyl heptanoate, myristyl nonanoate, lauryl heptanoate, lauryl octanoate, lauryl nonanoate, palmityl heptanoate, palmityl octanoate, and palmityl nonanoate. A typical ester of a short-chain saturated fatty acid for emollient use in the emulsified cosmetic composition can be myristyl octanoate.

A preferred emulsifier can be a glyceryl ester selected from the group consisting of glyceryl stearate, glyceryl palmitate, and glyceryl arachidate. A typical glyceryl ester for use in the emulsified cosmetic composition is glyceryl stearate. Other preferred emulsifiers include triethanolamine and 3-cyclohexene-1-methanol, alpha, 4-d imethyl-alpha-(4-methyl-3-pentenyl) ("bisabolol").

Pigment

The cosmetic or pharmaceutical composition can include at least one pigment for coloration, preferably red iron oxide The formulation examples below are included for illustrative purposes only and shall not limit the scope of the invention.

FORMULATION EXAMPLES

Example 1

Lightening & Decongestant Eye Mask (Rinse Off)

Mix A and stir until completely dispersed and soaked. Add B under stirring and adjust pH value to 5.5 with C.

| Phase | Material Name | Mixed INCI | Supplier | % (w/w) Material |
|---|---|---|---|---|
| A | DEIONIZED WATER | WATER | N.A. | 89.8 |
| A | PHENYLETHYL ALCOHOL NAT. | PHENYLETHYL ALCOHOL | DR STRAETMANS | 0.6 |
| A | CARBOPOL ULTREZ 21 | ACRYLATES/C10-30 ALKYL ACRYLATE CROSSPOLYMER | LUBRIZOL | 0.5 |
| A | HISPAGEL 200 Ns | GLYCERIN GLYCERYL POLYACRYLATE | BASF | 5.0 |

-continued

| Phase | Material Name | Mixed INCI | Supplier | % (w/w) Material |
|---|---|---|---|---|
| B | F111 | BELLIS PERENNIS (DAISY) FLOWER EXTRACT HIERACIUM PILOSELLA EXTRACT | CLR | 3.0 |
| C | NAOH (10%) | WATER SODIUM HYDROXIDE | N.A. | 1.1 |
| | | | | 100.0 |

Example 2

Anti Dark Circle Eye Lotion

Mix A in the given order and stir until uniform slowly. Add B and to A while stirring. Add C and stir until homogenous.

| Phase | Material Name | Mixed INCI | Supplier | % (w/w) Material |
|---|---|---|---|---|
| A | DEIONIZED WATER | WATER | N.A. | 85.49 |
| A | HYDROLITE-5 | PENTYLENE GLYCOL | SYMRISE | 5.00 |
| A | TEGO CARBOMER 141 | CARBOMER | EVONIK | 0.20 |
| B | MPC—MILK PEPTIDE COMPLEX | WHEY PROTEIN | CLR | 0.50 |
| B | NAOH (10%) | WATER SODIUM HYDROXIDE | N.A. | 0.81 |
| C | PROBIOBALANCE CLR NP | WATER LACTOSE MILK PROTEIN BIFIDA FERMENT LYSATE | CLR | 5.00 |
| C | F111 | BELLIS PERENNIS (DAISY) FLOWER EXTRACT HIERACIUM PILOSELLA EXTRACT | CLR | 3.00 |
| | | | | 100.00 |

Example 3

Brightening Facial Cream (O/W)

Add A and stir until completely dispersed. Mix B, heat up A and B to 75° C.-80° C. separately. Add B to A while stirring. Homogenize for 2 minutes with Ultra Turrax. Cool down while stirring and add C at room temperature. Adjust pH value to 5.0 with D as desired.

| Phase | Material Name | Mixed INCI | Supplier | % (w/w) Material |
|---|---|---|---|---|
| A | DEIONIZED WATER | WATER | N.A. | 69.9 |
| A | KELTROL CG-BT | XANTHAN GUM | CP KELCO | 0.1 |
| A | NAVIANCE MAIZE | ZEA MAYS (CORN) STARCH WATER | AKZO NOBEL | 2.0 |
| B | TEGO CARE 450 | POLYGLYCERYL-3 METHYLGLUCOSE DISTEARATE | EVONIK | 3.0 |
| B | TEGO ALKANOL 1618 | CETEARYL ALCOHOL | EVONIK | 1.5 |
| B | TEGOSOFT MM | MYRISTYL MYRISTATE | EVONIK | 1.0 |
| B | TEGOSOFT CR | CETYL RICINOLEATE | EVONIK | 3.0 |
| B | CETIOL CC | DICAPRYLYL CARBONATE | BASF | 3.0 |
| B | CETIOL OE | DICAPRYLYL ETHER | BASF | 4.0 |
| B | MYRITOL 318 | CAPRYLIC/CAPRIC TRIGLYCERIDE | BASF | 9.0 |

-continued

| Phase | Material Name | Mixed INCI | Supplier | % (w/w) Material |
|---|---|---|---|---|
| C | F111 | BELLIS PERENNIS (DAISY) FLOWER EXTRACT HIERACIUM PILOSELLA EXTRACT | CLR | 3.0 |
| C | MICROCARE SB | WATER SODIUM BENZOATE POTASSIUM SORBATE | THOR | 0.5 |
| D | NAOH (10%) | WATER SODIUM HYDROXIDE | N.A. | q.s |
| | | | | 100.0 |

Example 4

Night Lifting Eye Care (Leave On)

Mix A and stir until completely soaked. Add B and stir for a short. Add C and stir until uniform. Adjust pH value to 6-6.5 with D.

| Phase | Material Name | Mixed INCI | Supplier | % (w/w) Material |
|---|---|---|---|---|
| A | DEIONIZED WATER | WATER | N.A. | 79.95 |
| A | GLYCERIN 86% | GLYCERIN WATER | GUSTAV HEESS | 2.00 |
| A | HYDROLITE-5 | PENTYLENE GLYCOL | SYMRISE | 5.00 |
| A | COSMEDIA SP | SODIUM POLYACRYLATE | BASF | 1.20 |
| B | CETIOL J 600 | OLEYL ERUCATE | BASF | 8.00 |
| | COPHEROL F 1300 C | TOCOPHEROL | BASF | 0.01 |
| C | MPC—MILK PEPTIDE COMPLEX | WHEY PROTEIN | CLR | 0.50 |
| C | F111 | BELLIS PERENNIS (DAISY) FLOWER EXTRACT HIERACIUM PILOSELLA EXTRACT | CLR | 3.00 |
| D | NAOH (10%) | WATER SODIUM HYDROXIDE | N.A. | 0.34 |
| | | | | 100.00 |

The disclosure of all patents, publications, including published patent applications referenced in the specification are specifically incorporated by reference in their entirety to the same extend as if each such individual patent, publication or published patent application were specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the present invention/following claims.

The invention claimed is:

1. An herbal composition comprising a mixture of a) components obtained from *Bellis perennis* by a solvent extraction or a pressed juice process and b) components obtained from *Hieracium pilosella* by a solvent extraction or a pressed juice process, wherein the a) components and the b) components are present in the mixture in a ratio of 1:1 to 3:1 (w:w), and wherein the mixture of a) components and b) components is present in an amount effective for treatment or reduction of formation of dark circles to an eye area of a person in need of the treatment or reduction of formation of dark circles to an eye area, wherein the dark circles are not caused by excess epidural pigmentation of the skin.

2. The herbal composition according to claim 1, having a pH-value of between about pH 3 to 7.5.

3. The herbal composition according to claim 1, wherein the mixtures of a) components and b) components are alcoholic, glycolic or aqueous extracts.

4. The herbal composition according to claim 1, wherein the mixtures of a) components and b) components are press juices.

5. The herbal composition according to claim 1, wherein the mixture of a) components and b) components are obtained from a mixture of the starting plants.

6. The herbal composition according to claim 1, wherein at least one of the a) components, the b) components, or the mixture of a) components and b) components have been subjected to fermentation.

7. The herbal composition according claim 6, wherein said fermentation is *Lactobacillus, Bifidobacter* or *Lactococcus* fermentation.

8. The herbal composition according to claim 1, wherein the composition is formulated for topical application.

9. The herbal composition according to claim 8, wherein the composition is formulated as a cream, an ointment, an emulsion, a tonic, stick, dispersion, a formulation comprising a surfactant cleanser, a solution, a micellar water, a gel, a mask, a moist tissue pad or moist tissue mask.

10. The herbal composition according to claim 1, wherein the composition comprises 1 to 10% (w/w) of the mixture of a) components and b) components.

11. The herbal composition according to claim 1, wherein the composition comprises 1 to 50% (w/w) of the mixture of a) components and b) components.

12. The herbal composition according to claim 1, wherein the components are obtained from each of the *Bellis perennis* and *Hieracium pilosella* plants separately and then combined.

13. The herbal composition according to claim 1, wherein the composition has a pH-value of from about pH 4.0 to 6.5.

14. The herbal composition according to claim 1, wherein the composition comprises 10 to 30% (w/w) of the mixture of a) components and b) components.

15. The herbal composition according to claim 1, wherein the composition is formulated as a pharmaceutical formulation.

16. The herbal composition according to claim 1, wherein the composition is formulated as a cosmetic formulation.

17. A method of treatment or reduction of formation of dark circles under the eyes and/or puffy eyes/puffiness comprising application of the herbal composition of claim 5 to an eye area of a person in an amount effective to treat or reduce formation of dark circles under the eyes and/or puffy eyes/puffiness, wherein the dark circles are not caused by excess epidural pigmentation of the skin.

18. The method according to claim 17, wherein the dark circles under the eyes and/or puffiness are caused by any one of heredity, allergies, sleep deprivation/fatigue, oversleeping, eczema, contact dermatitis, hay fever/allergic rhinitis, stress, thinning skin and/or loss of fat and collagen with age, iron deficiency, minor trauma, crying, life style choices, fluid retention, excessive exposure to the sun, rubbing and scratching of eyes and medication.

19. The method according to claim 17, wherein the dark circles under the eyes and/or puffiness are caused by any one of thinning skin and/or loss of fat and collagen with age, life style choices, fluid retention, and influence of circadian rhythm by life style and life conditions.

20. The method according to claim 17, wherein the method comprises reduction of periorbital dark circles and/or periorbital edema, and wherein the herbal composition used in the method acts as an autophagy stimulator, heme oxygenase activator or VEGF-C production trigger.

* * * * *